United States Patent
Kaufmann et al.

(10) Patent No.: US 8,043,353 B2
(45) Date of Patent: Oct. 25, 2011

(54) DELIVERY SYSTEM HAVING A SELF-EXPANDING BRAIDED STENT

(75) Inventors: Ralf Kaufmann, Rangendingen (DE); Berthold Hauser, Burladingen (DE)

(73) Assignee: JOTEC GmbH (DE)

( * ) Notice: Subject to any disclaimer, the term of this patent is extended or adjusted under 35 U.S.C. 154(b) by 301 days.

(21) Appl. No.: 11/933,712

(22) Filed: Nov. 1, 2007

(65) Prior Publication Data

US 2008/0288043 A1 Nov. 20, 2008

Related U.S. Application Data

(63) Continuation of application No. PCT/EP2006/004026, filed on Apr. 28, 2006.

(30) Foreign Application Priority Data

May 4, 2005 (DE) .......................... 10 2005 020 785

(51) Int. Cl.
*A61F 2/06* (2006.01)
(52) U.S. Cl. ...................................... 623/1.11
(58) Field of Classification Search ................ 623/1.11, 623/1.12, 1.23; 606/181, 182, 167, 108
See application file for complete search history.

(56) References Cited

U.S. PATENT DOCUMENTS

| | | | |
|---|---|---|---|
| 3,350,127 A | 10/1967 | Hekelaar | |
| 4,360,016 A * | 11/1982 | Sarrine | 600/576 |
| 5,147,375 A * | 9/1992 | Sullivan et al. | 606/182 |
| 5,433,723 A * | 7/1995 | Lindenberg et al. | 606/198 |
| 5,591,172 A * | 1/1997 | Bachmann et al. | 623/1.11 |
| 5,700,269 A | 12/1997 | Pinchuk et al. | |
| 6,350,278 B1 * | 2/2002 | Lenker et al. | 623/1.12 |
| 6,443,979 B1 * | 9/2002 | Stalker et al. | 623/1.11 |
| 7,182,779 B2 * | 2/2007 | Acosta et al. | 623/1.11 |
| 2004/0193252 A1 * | 9/2004 | Perez et al. | 623/1.23 |
| 2005/0027345 A1 | 2/2005 | Horan et al. | |
| 2006/0184238 A1 | 8/2006 | Kaufmann et al. | |

FOREIGN PATENT DOCUMENTS

| | | |
|---|---|---|
| DE | 1 975 097 | 12/1967 |
| DE | 103 35 649 | 2/2005 |
| EP | 0 943 300 | 9/1999 |
| WO | WO 96/32078 | 10/1996 |
| WO | WO 96/36298 | 11/1996 |
| WO | WO 03/030783 | 4/2003 |
| WO | WO 2004/024034 | 3/2004 |

* cited by examiner

*Primary Examiner* — Tom Hughes
*Assistant Examiner* — Jonathan W Miles
(74) *Attorney, Agent, or Firm* — Klarquist Sparkman, LLP

(57) ABSTRACT

An insertion system with a self-expanding braided stent (11) for implantation in a blood vessel has an outer sleeve (12) with a distal end (14) and a proximal end. An inner sleeve (16) arranged in the outer sleeve (12) is displaceable relative to the latter and protrudes, with a handling section, from the proximal end of the outer sleeve (12). Moreover, at the distal end (15), there is a tip (18) which is securely connected to a stent support (24) on which the braided stent (11) is arranged in its loaded state. The stent support (24) is arranged to be displaceable relative to the inner sleeve (16).

19 Claims, 9 Drawing Sheets

DELIVERY SYSTEM HAVING A SELF-EXPANDING BRAIDED STENT

CROSS REFERENCE TO RELATED APPLICATIONS

This is a continuation application of International Patent Application PCT/EP2006/004026, filed Apr. 28, 2006, designating the United States and published in German as WO 2006/117167 A1, which claims priority to German application number DE 10 2005 020 785.5, filed May 4, 2005.

BACKGROUND OF THE INVENTION

1. Field of the Invention

The present invention relates to a delivery system having a self-expanding braided stent intended for implantation into a blood vessel, with an outer sleeve, which has a distal end and a proximal end and in which an inner sleeve is arranged that is displaceable relative to the outer sleeve and protrudes, with a handling portion, from the proximal end of the outer sleeve, and with a tip, which is arranged at the distal end and is securely connected to a stent support on which the braided stent is arranged in its loaded state.

2. Related Prior Art

A delivery system of this kind is known commercially to the applicant of the present invention.

A stent is understood as a radially expandable endoprosthesis, which is a typical intravascular implant that is implanted via a lumen and is radially enlarged expanded after it has been introduced percutaneously. Stents are used, for example, to strengthen blood vessels and, in the vascular system, to prevent restenosis after angioplasty. In addition, they are also implanted in arteries for the treatment of aneurysms.

Such stents can be self-expanding or can be expanded by a radial force applied from the inside, for example when they are fitted on a balloon.

A very wide variety of stents are used depending on the type of application. The present invention is concerned with the application of what are called braided stents, such as are known, for example, from DE 197 50 97 A1 or DE 103 35 649 A1.

A braided stent is a metal stent that is produced by what is called a plain weaving technique. It is composed of a hollow body, which can stretch in the longitudinal direction and whose jacket is a braid made up of a multiplicity of filament-like elements which, in the expanded state of the braided stent, intersect a plane, perpendicular to the longitudinal direction, at a braid angle. A braided stent undergoes a considerable change in length when stretched, this change in length being all the greater the greater the original diameter and the smaller the original braid angle.

For implantation, a braided stent of this type is stored in an elongate configuration in what is called a delivery system or applicator, the latter being introduced percutaneously into the body at a suitable location, for example the femoral artery, and being guided through a lumen as far as the vessel where the stent is to be released. The delivery system and the stent are often provided with X-ray markers with which the positioning and the release of the stent can be monitored in situ.

In stents that experience no change or only a very slight change in length when released, the position of the implantable stent can be verified in this way without any difficulty, for which reason there are also many different delivery systems available for stents of this type that only expand radially.

In braided stents, however, a problem that arises is that they are very much shortened when released. At a braid angle of 40°, for example, the ratio between the stent length in the loaded state in the delivery system and the stent length in the expanded state, in other words the free state, is 1.5:1, for example. If the braid angle $\alpha$ is smaller, this ratio increases still further, and, at a braid angle of $\alpha=10°$, the ratio can even be 4:1 to 6:1. It should be noted here that the shortening in length is of course also dependent on the diameter of the stent in the loaded state and on the diameter of the stent in the released state.

Braided stents are therefore extremely extensible and, in their elongated state, they as it were store mass which, upon contraction of the stents, ensures a compact and stiff functional area, as is explained in detail in aforementioned DE 103 35 649 A1.

Braided stents, in which this shortening has to be taken into account, have hitherto been releasable in the blood vessel only with a low level of positioning accuracy. However, the positioning of a stent at the desired location in the blood vessel is a critical factor that determines the effect of the stents and the success of the medical intervention. The area in the blood vessel where the stent is to be expanded is usually accessible to the physician only with difficulty.

For example, the stent has to be positioned in the area of an organ or, in the case of the carotid artery, in the region of the cerebral arteries, where in some cases only a relatively short stent has to be put in place. However, because of the considerable shortening that takes place upon release of a braided stent, conventional systems require a substantial length of release, as is the case, for example, in the system available on the market.

In the known delivery system, the braided stent in the loaded state, that is to say in the extremely elongated form, lies proximally from the tip and rests on the stent support, which is connected securely to the inner sleeve. The stent is pressed radially inward by the outer sleeve and is held in its elongated form.

To deploy the braided stent, the inner sleeve is held secure, and with it the stent support and the tip connected to the latter, and it must not be moved during the release. The outer sleeve is then pulled back carefully from the tip, such that the stent is released gradually. As the stent comes free, it contracts in the direction of the outer sleeve and thus moves away from the tip, which remains fixed in position relative to the vessel by the inner sleeve. As the outer sleeve is pulled back, the gradually released and radially expanding stent, contracting in the longitudinal direction, follows the outer sleeve until a portion of the braided stent has been released which is such that the latter bears securely against the inner wall of the vessel.

All of this means, however, that the tip of the delivery system has to be displaced distally far beyond the intended site of release of the braided stent in order to permit a correct placement. In the known delivery system, this amounts to several centimeters, which leads to a length of release that cannot be tolerated, especially in the case of small braid angles. Particularly in cases where a relatively short stent has to be placed in proximity to an organ or to the cerebral arteries, there is a danger that the further advanced tip will cause damage to the organ or the cerebral artery.

A further disadvantage of the known delivery system is seen in the fact that the position of the braided stent in the vessel can be influenced only with difficulty by manipulation of the outer sleeve. If the operating surgeon has pushed the delivery system in too far or not far enough, he can no longer influence the final position of the braided stent in the known delivery system. If he finds that the braided stent is released too far above or below the planned site of deployment, he has to pull the braided stent in again, which, in the known delivery system, can only be done in emergency situations, and not more than twice. To "reload" the braided stent into the delivery system, the outer sleeve is now held secure, while the inner sleeve is carefully pulled back. In the known delivery system, however, this reloading is only possible as long as not more than 50% of the braided stent has been released.

In the known delivery system, therefore, one disadvantage is that braided stents in particular with small braid angles cannot be positioned close enough to organs or cerebral arteries, etc., while a further disadvantage is that exact positioning is extremely difficult.

SUMMARY OF THE INVENTION

Against this background, an object of the present invention is to further develop the known delivery system in such a way that, by simple structural means, braided stents can be released with improved accuracy of positioning, and the length of release is preferably reduced.

In the braided stent mentioned at the outset, this object is achieved according to the invention by the fact that the stent support is arranged to be displaceable relative to the inner sleeve.

The object of the invention is achieved completely in this way.

The inventors of the present application have in fact found that the problems of the known delivery system are attributable, among other things, to the fact that the stent support is part of the inner sleeve. According to the invention, however, the stent support is now separate from the inner sleeve, such that the braided stent can be released either by pulling the outer sleeve back or by advancing the inner sleeve. In contrast to the known braid system, the inner sleeve can now be displaced relative to the stent support.

Thus, according to the invention, the stent is released by the relative movement between outer sleeve and inner sleeve, and the operating surgeon can therefore also manipulate the outer sleeve and change the position of the stent in situ if he notices, during release, that he has not yet pushed the delivery system in far enough or has already pushed it in too far.

At the start of the release of the braided stent, the relative movement between outer sleeve and inner sleeve first of all causes the tip to come free from the outer sleeve, and the distal end of the stent also emerges from the outer sleeve and expands, in other words comes free from the tip. By advancing the inner sleeve, the stent is now pushed down from the stent support, such that the stent can slide past the tip, since the latter is no longer coupled to the inner sleeve. During release, it may be advisable first to pull the outer sleeve back slightly, until the stent comes free from the tip, and then to advance the inner sleeve. By alternate working with inner sleeve and outer sleeve or by joint displacement of inner sleeve and outer sleeve, the stent can now be positioned optimally. Although the considerable shortening during release also leads in this case to a shifting of the stent that cannot be precisely predicted, this shifting can nevertheless be compensated by relative movements in both directions.

Moreover, since the tip does not protrude distally past the desired site of release, or does so only slightly, there is also no danger of damage to vessels or organs situated distally from the site of deployment.

In addition, by means of this new handling possibility, the stent can be correctly "structured", that is to say it can have different degrees of compactness at different locations, for example in order to generate a very compact metal structure particularly in the area of an aneurysm, whereas it is more extended in front of and behind the aneurysm, such that it can anchor itself securely against the inner walls of the vessel.

By separating the tip and the stent support from the inner sleeve, the novel delivery system therefore also allows braided stents that undergo extreme shortening during release to be positioned at previously inaccessible locations in vessels, and the novel delivery system also allows the properties of the braided stents to be used optimally, namely by means of the braided stents also being able to be suitably structured or elongated at the time of their release.

In a further embodiment, between outer sleeve and stent support, a locking mechanism is provided by which the movement of the stent support relative to the outer sleeve in the distal direction is limited to a maximum path of travel.

The advantage of this measure is that the tip is not advanced too far upon the initial release of the braided stent. A further advantage is that, during the further release of the braided stent by pulling the outer sleeve back, the tip is pulled back too, that is to say in the proximal direction into the expanding stent. This measure also has the effect that, when the inner sleeve is advanced relative to the outer sleeve, the stent support and therefore the tip remain stationary, thus ensuring that the braided stent can as it were be pushed over the tip.

This measure thus allows the braided stent to be deployed in the distal direction ahead of the original position of the tip. For this purpose, the delivery system is pushed into the vessel until the tip is situated just in front of the site at which the released stent is to end distally. The outer sleeve is now pulled back slightly, such that the tip and the braided stent come free at its distal end. The inner sleeve is then advanced, as a result of which the stent slides past the tip, such that its distal end passes distally from the tip and it is in contact with the inner wall of the blood vessel. In certain cases this sequence can also be reversed, such that the inner sleeve is first advanced until the braided stent bears on the blood vessel, whereupon the outer sleeve is then pulled back, or a further relative movement takes place between outer sleeve and inner sleeve.

By means of further relative movements between outer sleeve and inner sleeve, the braided stent can now be suitably structured and deployed. This means that the tip does not have to be advanced into areas of the vessel where the stent does not come to lie after its final release. This is a decisive advantage over the known release systems.

In a further embodiment, the locking mechanism limits the movement of the stent support relative to the outer sleeve in the proximal direction when the stent support has previously been moved relative to the outer sleeve in the distal direction by a predetermined path of travel.

The advantage of this measure is that the braided stent, even when almost fully released, can be completely reloaded. When the stent, suitably connected to the inner sleeve for this purpose, is pulled back, the tip is not entrained with it, and instead it is held secure relative to the outer sleeve by the locking mechanism, such that the relative movement between stent support and inner sleeve is again possible. In this way, the braided stent is as it were pulled back onto the stent support, and the locking of the tip means that the braided stent does not jam between outer sleeve and tip.

Although it would also be possible to permit the relative movement between stent support and inner sleeve by means of different frictional forces or by springs, it has been found that, with the small dimensions and diameters present in the novel delivery system, a purely mechanical locking represents a better solution.

In the novel delivery system, therefore, the tip and the stent support are freely movable relative to the outer sleeve and also relative to the inner sleeve, and suitable measures can be taken in order to limit the displaceability of the stent support relative to the outer sleeve both in the distal direction and also in the proximal direction. Although this limiting of the freedom of movement can be effected by spring forces or frictional forces, locking mechanisms are used for this purpose in a preferred embodiment of the invention.

In yet another embodiment, an unlocking mechanism is connected to the inner sleeve and, upon proximal movement of the inner sleeve relative to the outer sleeve, again frees the movement of the stent support relative to the outer sleeve.

The advantage of this is that the locking of the movement of the stent support relative to the outer sleeve in the proximal direction is finally cancelled again, such that the tip can then be pulled back again as far as the outer sleeve if the stent has previously been pulled back completely onto the stent support. This permits renewed positioning of the entire delivery system in the distal or proximal direction and permits simple and complete removal of the already partially released stent, if this is indicated during the operation.

In addition, it is possible in this way, after complete release of the stent, to pull the tip back in the proximal direction into the outer sleeve before the delivery system is finally pulled back out of the body.

According to a further embodiment, the stent support is connected at its proximal end to a control rod, which extends centrally through the inner sleeve and protrudes at the proximal end from the inner sleeve.

The advantage of this is that the control rod allows the stent support and thus the tip to be actively moved in translation relative to the inner sleeve and to be secured, such that locking and unlocking mechanisms can be dispensed with. If so desired, the locking mechanism and if appropriate the unlocking mechanism can also be provided here in the area of the proximal end, such that they remain outside the body. It must be borne in mind, however, that the operating surgeon also has to manipulate the control rod in addition to the outer sleeve and inner sleeve in this construction.

Alternatively, in another embodiment, the stent support is mounted at its proximal end in the inner sleeve, which has a longitudinal slit through which a first limit stop connected to the outer sleeve protrudes into the inner sleeve, by means of which limit stop the movement of the stent support relative to the outer sleeve in the distal direction is limited to the maximum path of travel.

The advantage of this measure is that the freely movable tip and the stent support connected thereto are as it were designed without their own drive, the limit stop acting only in the distal direction. The maximum path of travel by which the tip can therefore be moved in the distal direction relative to the outer sleeve is defined by the axial distance between this first limit stop and an abutment surface on the stent support, when the stent is still in the loaded state.

In a further embodiment, the stent support is securely connected to a distal control block, which is mounted displaceably in the inner sleeve and which is connected under tension to a proximal control block mounted displaceably in the inner sleeve, which proximal control block comes into contact with the first limit stop upon movement of the stent support relative to the outer sleeve in the distal direction by the maximum path of travel.

This measure is advantageous from the point of view of construction, since the locking mechanism acting in the distal direction is of a simple structure and the two control blocks can be easily installed by micro-mechanical means in the lumen that is present anyway in the inner sleeve.

According to a further embodiment, the longitudinal slit is assigned a further limit stop, which is connected to the stent support and which comes into contact with a recess on the outer sleeve and limits the movement of the stent support relative to the outer sleeve in the proximal direction when the stent support has previously been moved relative to the outer sleeve by the predetermined path of travel in the distal direction.

This measure too is advantageous from the point of view of construction. The further limit stop is initially held in the inner sleeve, and it is only when the inner sleeve has been further displaced distally relative to the stent support that the further limit stop comes free and can engage into the outer sleeve through the longitudinal slit in the inner sleeve, thus ensuring that, when the stent is pulled back by means of the inner sleeve being pulled back, the tip is not pulled in the proximal direction into the outer sleeve by the friction between stent support and stent.

In a further embodiment, the further limit stop is arranged on the distal control block.

The advantage of this is that the longitudinal slit in the inner sleeve can be used to unlock the further limit stop. When the inner sleeve is pulled back, the distal end of the longitudinal slit provided in the inner sleeve presses the further limit stop inward, such that it comes free from the outer sleeve, and the tip is now pulled into the outer sleeve. Since the further limit stop is arranged on the distal control block, the unlocking also follows automatically only when the inner sleeve has been pulled back almost completely to its original position again, and the braided stent has thus been pulled safely back onto the stent support.

According to yet another embodiment, the distal and proximal control blocks are connected to each other by a connecting wire, which preferably extends through a guide hole provided in the first limit stop.

In this measure too, the simple construction is of advantage, since only two control blocks need be arranged in the inner sleeve, and, since it is guided through the guide hole, the connecting wire cannot buckle or become knotted even when the tip is finally pulled back.

In a further embodiment, the distal and proximal control blocks are formed at opposite ends of a control sleeve, which is mounted displaceably in the inner sleeve and in which a longitudinal slit is provided into which the first limit stop engages.

This is an alternative to the solution with the connecting wire and is likewise of a simple construction. A further advantage is that the proximal control block is also entrained when the inner sleeve is pulled back.

In other embodiments of the invention, a longitudinally displaceable slide body is arranged on the stent support and lies between the braided stent and the tip when the braided stent is in the loaded state.

The advantage of this measure is that, surprisingly, jamming of the braided stent between outer sleeve and tip or slide body is avoided if the braided stent is reloaded. The slide body therefore represents an alternative or a complement to the locking mechanism that limits the movement of the stent support relative to the outer sleeve in the proximal direction when the stent support has previously been moved relative to the outer sleeve by a predetermined path of travel in the distal direction.

The inventors of the present application have in fact found that this slide body performs a kind of oscillating movement between tip and braided stent when the stent is pulled back onto the stent support; it is briefly clamped and then springs back in the direction of the tip, whereupon the braided stent can then be pulled in further. This also has the effect that an almost completely released braided stent can be reloaded again.

According to a further embodiment, the slide body has an external diameter that is greater than the difference between the internal diameter of the outer sleeve at its distal end and twice the wall thickness of the braided stent.

This measure is of advantage from the point of view of construction, since it ensures that the braided stent cannot jam so easily between slide body and outer sleeve.

In a further embodiment, the slide body is rounded at its proximal end and is preferably made of a material that has a low coefficient of kinetic friction relative to the inner wall of the braided stent, the slide body further preferably being made of an elastic material.

These measures, individually and in combination, also have the effect that the braided stent does not jam so easily between the slide body and the distal end of the outer sleeve, and a slide body made of elastic material springs back after possible clamping, since it converts the stored elastic deformation energy almost completely into kinetic energy and springs back axially in the distal direction.

According to yet another embodiment, the distal end of the outer sleeve is stiffened.

This can be done using X-ray markers, for example, which strengthen the distal end of the outer sleeve, such that the latter cannot widen. This also has the effect that the braided stent cannot jam between the slide body and the distal end of the outer sleeve when pulled back.

According to another embodiment, a spacer is fixed on the handling portion of the inner sleeve and limits the sliding of the inner sleeve into the outer sleeve.

This measure is of advantage from the point of view of construction, since it is a simple way of providing a safety element in the operation of the novel delivery system. The spacer is in fact applied in such a way that it indicates when the stent is just before the final release. It has to be removed before the release can be completed. Therefore, as long as the operator does not remove this spacer, he cannot release the braided stent to such an extent that the latter can no longer be pulled back.

According to yet another embodiment, the inner sleeve has a holder at its distal end, via which holder the proximal end of the braided stent is connected under tension to the inner sleeve.

The advantage of this measure is that it permits simple reloading of the stent, which can be pulled onto the stent support again by means of the inner sleeve being pulled back.

In a further embodiment, the holder has a flange on which the proximal end of the braided stent is fixed by the outer sleeve.

This measure too is advantageous from the point of view of construction, since the flange constitutes a kind of barb that automatically comes free when the inner sleeve is pushed so far into the outer sleeve that the flange protrudes from the distal end of the outer sleeve. For this purpose, it may be necessary to remove the spacer from the inner sleeve beforehand.

A further advantage of this construction is that the proximal end of the stent is not damaged in the way it could be in the case of a holder device from which the braided stent has to be pulled out.

In a further embodiment, a channel for a guide wire extends centrally through the tip and the stent support, which guide wire is guided laterally out of the inner sleeve and outer sleeve through longitudinal slits.

This measure is known per se from the prior art, the guide wire being put in place before the actual insertion of the delivery system, so as to be able to guide the tip of the delivery system safely through the windings of the vessels. This method is generally known as the Seldinger technique.

Further advantages and features will become evident from the following description and from the attached drawing.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and are depicted in the drawing, in which.

DESCRIPTION OF PREFERRED EMBODIMENTS

Figure 1:
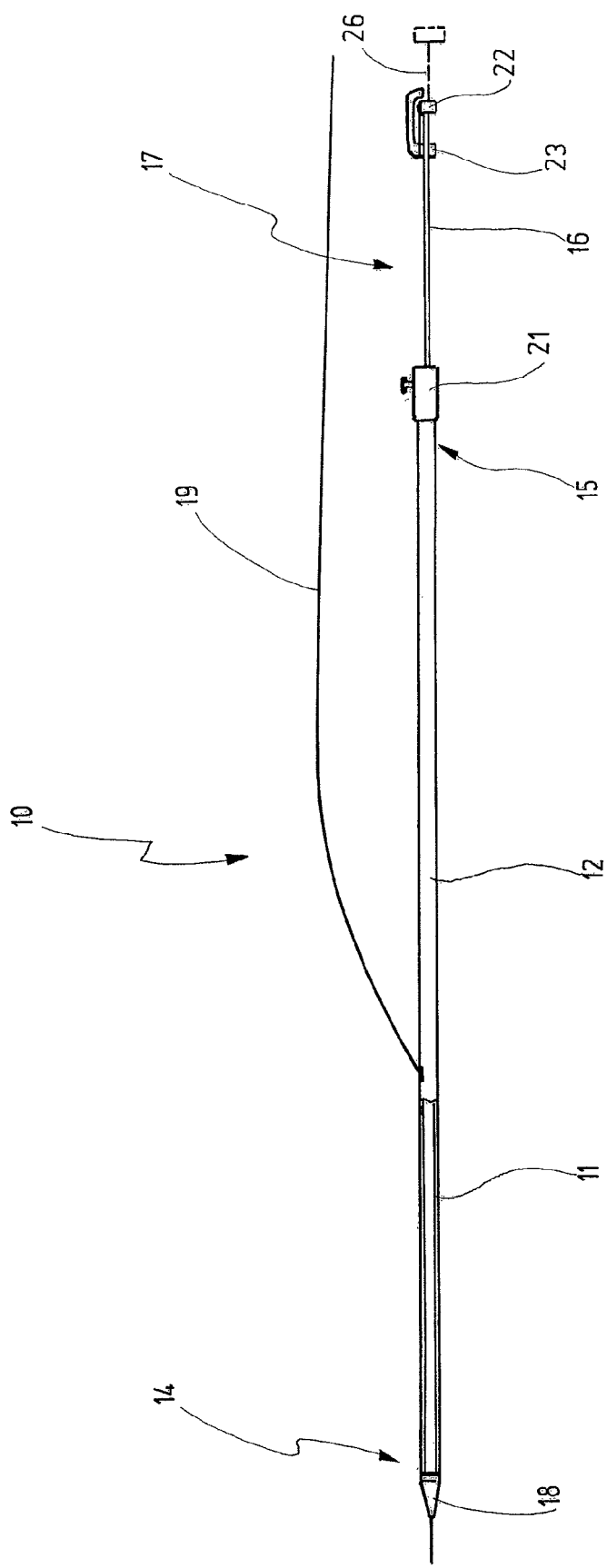
FIG. 1 shows a schematic side view of a delivery system for a braided stent.

In FIG. 1, reference number 10 schematically designates a delivery system with which a braided stent, indicated by reference number 11, can be implanted into a blood vessel.

The braided stent 11 is a self-expanding metal stent produced by a plain weaving technique, as is described in aforementioned DE 103 35 649. Because of its braid angle of α=10°, the braided stent 11, in the state when loaded into the delivery system 10 as shown in FIG. 1, has a length that is about five times longer than the length of the braided stent in the released state.

The delivery system 10 comprises an outer sleeve 12, on the distal end 14 of which the braided stent 11 is arranged, and an opposite proximal end 15.

In line with conventional terminology, distal direction designates a direction which is toward the patient and in which the braided stent 11 is to be implanted. Proximal direction accordingly designates a direction toward the operator.

An inner sleeve 16 is arranged in the outer sleeve 12 and is displaceable relative to the latter, said inner sleeve 16 protruding from the proximal end 15 of the outer sleeve 12 and having a handling portion 17 there.

At the distal end 14, the delivery system 10 has a tip 18 through which there extends a guide wire, designated by reference number 19, which protrudes laterally out of the outer sleeve 12. In accordance with the known Seldinger technique, this guide wire is used to insert the delivery system 10 into a blood vessel of a patient, in order to release the braided stent 11 there.

For the maneuvers required in this technique, a pull grip 21 with irrigation attachment is arranged at the proximal end 15 of the outer sleeve 12, in a manner generally known in delivery systems of this kind. The handling portion 17 of the inner sleeve 16 also has a grip 22 via which the inner sleeve 16 can be displaced relative to the outer sleeve 12. In front of the grip 22, in the distal direction, a spacer 23 is also indicated, which serves as a limit stop during the sliding of the inner sleeve 16 into the outer sleeve and comes into contact with the pull grip 21.

The spacer 23 prevents the inner sleeve 16 from being pushed so far into the outer sleeve 12 that the braided stent is fully released. It therefore represents a safety element that prevents the braided stent 11 from being released too early. When the spacer 13 is removed, the inner sleeve 16 can be pushed further into the outer sleeve 12, in order finally to release the braided stent 11.

Figure 2:
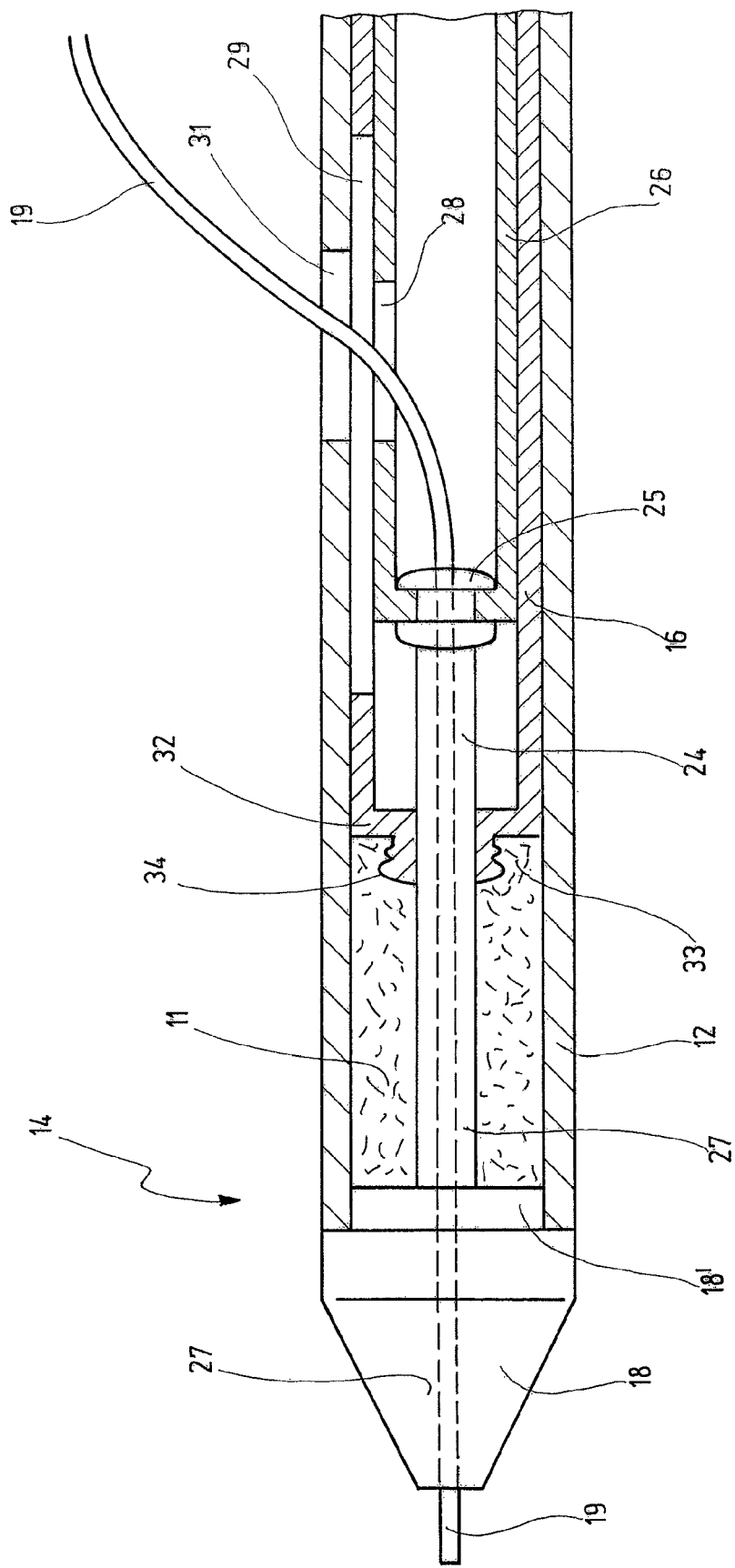
FIG. 2 shows an enlarged and schematic longitudinal section (not true to scale) through the distal portion of the delivery system from FIG. 1 in a first illustrative embodiment.

FIG. 2 shows an enlarged and schematic longitudinal section, not true to scale, through the delivery system 10 from FIG. 1.

The tip 18 rests with its flange 18' on the inside face of the outer sleeve 12, such that the interior of the outer sleeve 12 is closed off from the outside. In FIG. 2, the tip 18 is adjoined in the proximal direction by a stent support 24, which is securely connected to the tip 18 and protrudes into the inner sleeve 16 and is there securely connected at its proximal end 25 to a control rod 26, the latter extending centrally through the inner sleeve 16 and protruding from the inner sleeve 16 at the grip 22, as is indicated by broken lines in FIG. 1.

The tip 18 and the stent support 24 are both traversed by a channel 27 through which the guide wire 19 extends, said guide wire extending outward through longitudinal slits 28, 29 and 31 in the control rod 26, inner sleeve 16 and outer sleeve 31, respectively. The longitudinal slits 28, 29 and 31 are chosen such that the guide wire 19 does not buckle or jam during the displacement of the inner sleeve 16 relative to the outer sleeve 12 and during the displacement of the stent support 24 via the control rod 26.

At its distal end 32, the inner sleeve 16 has a holder via which the proximal end 33 of the braided stent 11 is connected under tension to the inner sleeve 16. For this purpose, a flange 34 is provided on the distal end 32 of the inner sleeve 16, on which flange 34 the proximal end 33 of the braided stent 11 sits and is held there by the radially inwardly directed pressure of the outer sleeve 12.

The construction in FIG. 2 is such that outer sleeve 12, inner sleeve 16 and stent support 24 are displaceable relative to one another. To release the braided stent 11, the outer sleeve 12 is first pulled back, for example, for which purpose the inner sleeve 16 and the control rod 26 are held firmly in place. In this way, the tip 18 comes free of the outer sleeve 12, such that the braided stent 11 can widen radially outward, while at the same time becoming shorter. Alternatively, it is also possible for the inner sleeve 16 first to be advanced relative to the outer sleeve 12 until the braided stent 11 positions itself on the blood vessel. The outer sleeve 12 is then pulled back in order to further release the braided stent 11.

For further release of the braided stent 11, the inner sleeve 16 can then be displaced relative to the outer sleeve 12, as a result of which the braided stent 11 is pushed down from the stent support 24. To ensure that the tip 18 is not pushed further in the distal direction because of the resulting friction between the braided stent 11 and the stent support 24, the control rod 26 is held immovably together with the outer sleeve 12. This can be done by the operator, in which case it is also possible, if required, to lock the control rod 26 and outer sleeve 12 on one another at the proximal end 15.

If the release of the braided stent 11 does not take place satisfactorily, the braided stent 11 can also be pulled back onto the stent support 24, specifically by pulling the inner sleeve 16 back into the outer sleeve 12. To ensure that the tip 18 does not jam against the stent pulled back into the outer sleeve 12, the tip 18 is now pushed and held so far in front of the outer sleeve 12, via the control rod 26, that the braided stent 11 can be pulled back without any problem into the outer sleeve 12 and onto the stent support 24.

In this way, it is even possible for the braided stent 11 to be reloaded completely into the delivery system 10, and for the tip 18 then to be pulled back in.

If indicated, the delivery system 10 can then be completely removed again, in which case it is also possible simply to correct the position of the delivery system in the blood vessel and then release the braided stent 11 again.

Figure 3:
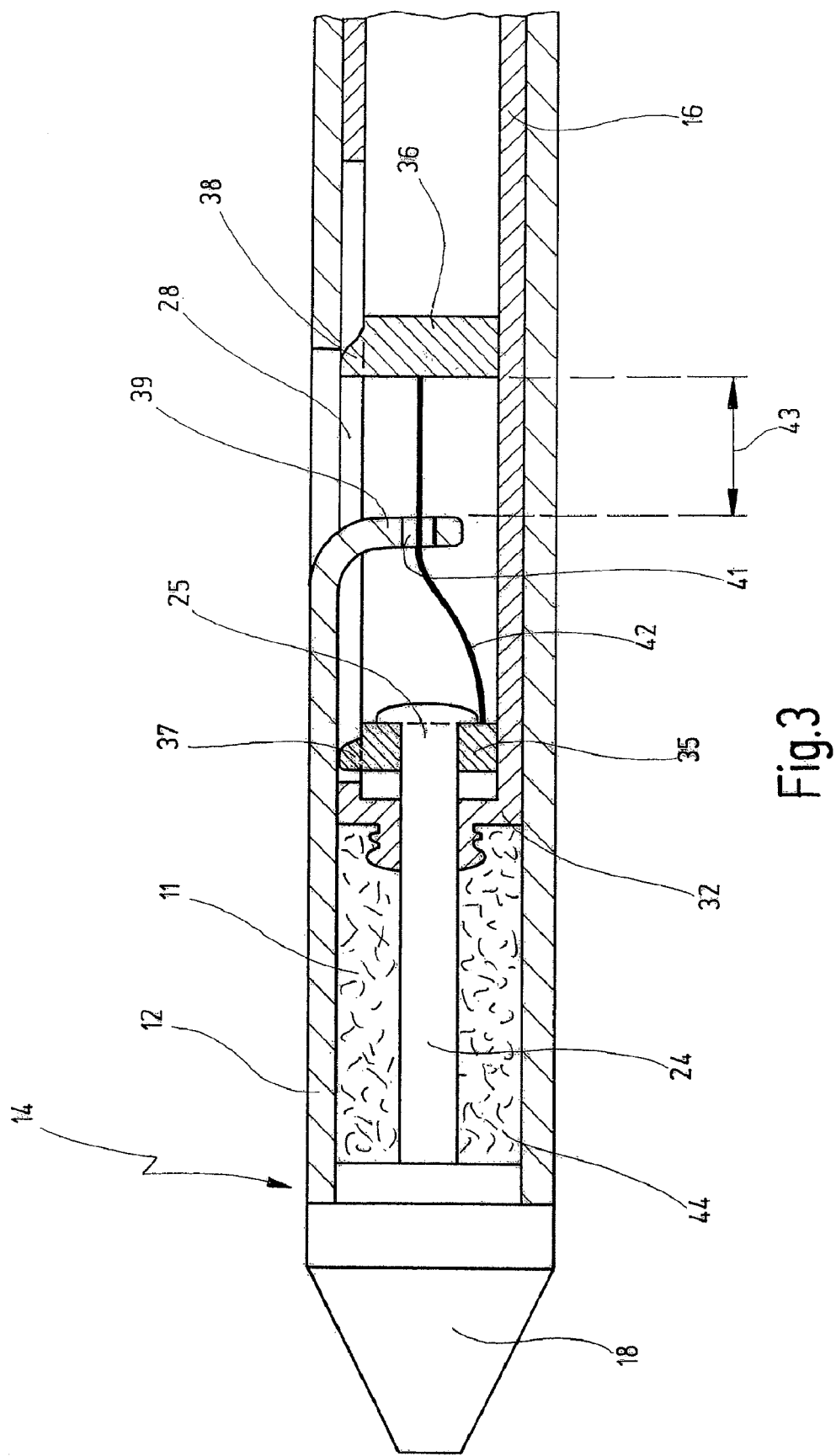
FIG. 3 shows, in a view similar to FIG. 2, a second illustrative embodiment of the novel delivery system.

In FIG. 3, which is a view similar to FIG. 2, but not depicting the guide wire 19, a second illustrative embodiment of the novel delivery system is shown in which active control of the translational movement of the tip 18 and thus of the stent support 24 is omitted, and the tip 18 is instead arranged to be freely movable with respect to the outer sleeve 12 and to the inner sleeve 16. For this purpose, the stent support 24, at its distal end in the inner sleeve 16, is mounted on a distal control block 35, to which a proximal control block 36 is assigned. The distal control block 35 and the proximal control block 36 are of a rotationally symmetrical design but have respective lugs 37, 38 with which they are guided in the longitudinal slit 28 of the inner sleeve 16, such that they cannot become jammed.

A limit stop 39 formed integrally with the outer sleeve 12 protrudes inward through the longitudinal slit 28 and is provided with a guide hole 41 through which a connecting wire 42 extends that connects the distal control block 35 and the proximal control block 36 to each other under tension.

Between the limit stop 39 and the distal control block 36, a free distance 43 is indicated by which the control block 36 and with it the control block 35 can be moved in the distal direction relative to the outer sleeve 12. Since the distal control block 35 is securely connected to the stent support 34 and the latter is securely connected to the tip 18, the clearance 43 thus also determines the maximum path of travel by which the tip 18 can be displaced relative to the outer sleeve 12 in the distal direction.

Figure 4:
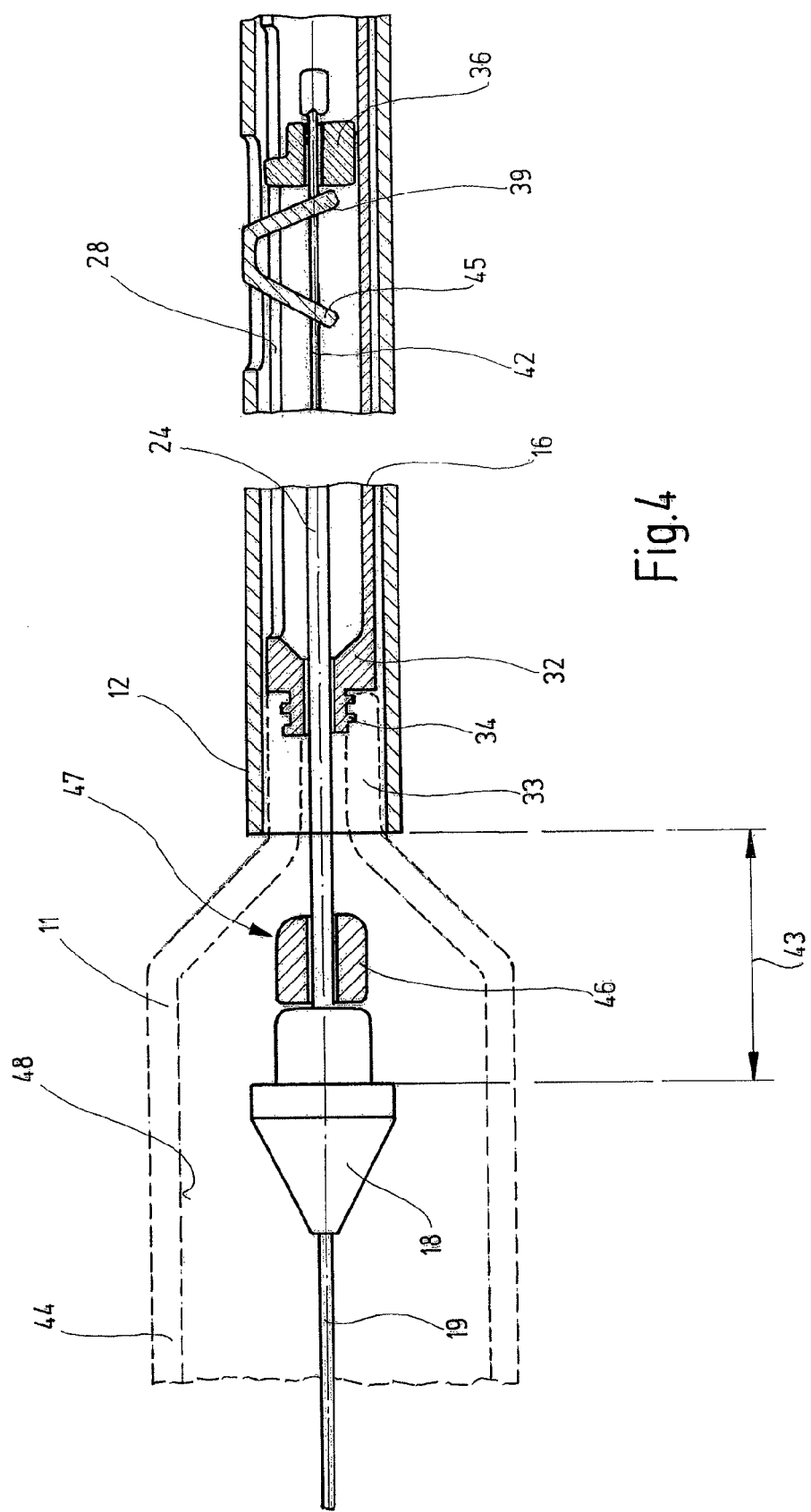
FIG. 4 shows, in a view similar to FIG. 2, but with the braided stent partially released, a third illustrative embodiment of the novel delivery system.

The control blocks 35 and 36 thus form, together with the connecting wire 42 and the limit stop 39, a locking mechanism by which the movement of the stent support 24 relative to the outer sleeve in the distal direction is limited to the maximum path of travel 43. As the braided stent 11 slides down from the stent support 34, the tip 18 thus moves at most by the path of travel 43 in the distal direction past the outer sleeve 12, as is shown schematically in FIG. 4. FIG. 4 shows, in a view similar to FIG. 3, another illustrative embodiment of the novel delivery system, but with the braided stent 11 already having been partially released, such that it protrudes with its distal end 44 in the distal direction beyond the tip 18. This is achieved by the fact that, after the delivery system has been positioned in the vessel, the outer sleeve 12 is first pulled back by the path of travel 43, or the inner sleeve 16 is advanced in the distal direction relative to the outer sleeve 12, such that the tip 18 is situated distally in front of the outer sleeve 12 by the path of travel 43. Then, by advancing the inner sleeve 16 in the distal direction, the braided stent 11 is gradually pushed down from the stent support 24, such that it widens radially and migrates with its distal end 44 distally past the tip 18.

If, in the situation shown in FIG. 4, the outer sleeve 12 is now pulled back, the braided stent 11 widens further in the proximal direction, in which process, however, it cannot grow much shorter, because it is held both at its distal end 44 and also at its proximal end 33. To now give the braided stent 11 a very compact structure, in other words to allow it to compress to the maximum extent in the axial direction, not only is the outer sleeve 12 pulled back, but at the same time, or instead, the inner sleeve 16 is also advanced, such that further stent material is as it were supplied from the remaining storage area of the braided stent 11.

In this way, it is possible, by displacement of outer sleeve 12 and inner sleeve 16 relative to one another, to deploy a braided stent 11 optimally in a vessel and, by suitable maneuvering, to ensure that compactly structured and less compactly structured areas of the braided stent 11 are alternately formed, as is desirable from the medical point of view.

This possibility is afforded in the delivery system 10 by the fact that the tip 18 is freely displaceable relative to the inner sleeve 16. If the inner sleeve 16 in FIG. 4 is pushed in the distal direction, this does not change the position of the tip 18. If, by contrast, the outer sleeve 12 is pulled in the proximal direction, the tip 16 is then also pulled back in the proximal direction. In this way, it is possible to guide the tip 18 directly to an organ or, for example, to a cerebral artery, and, upon releasing the braided stent 11, to push the latter still further in the distal direction beyond the tip 18.

This targeted positioning and targeted structuring of the braided stent in the blood vessel has not been possible with known delivery systems.

It will also be seen from the right-hand side of FIG. 4 that, in addition to the first limit stop 39, a bracket 45 is also connected to the outer sleeve 12, said bracket 45 permitting even better guidance of the connecting wire 42 in the interior of the inner sleeve 16.

If the braided stent 11 is now to be partially or completely pulled back into the outer sleeve 12, there is a danger of the friction between braided stent 11 and stent support 24 causing the latter to move in the proximal direction, with the result that the braided stent 11 can become jammed between outer sleeve 12 and tip 18. As is shown in FIG. 4, this can be avoided by providing a slide body 46 which is arranged on the stent support 24 and which, when the braided stent 11 is fully loaded, lies in the outer sleeve 12 between the tip 18 and the distal end 44 of the braided stent 11.

The slide body 46 is made of an elastic material and is rounded at its proximal end 47.

Figure 5:
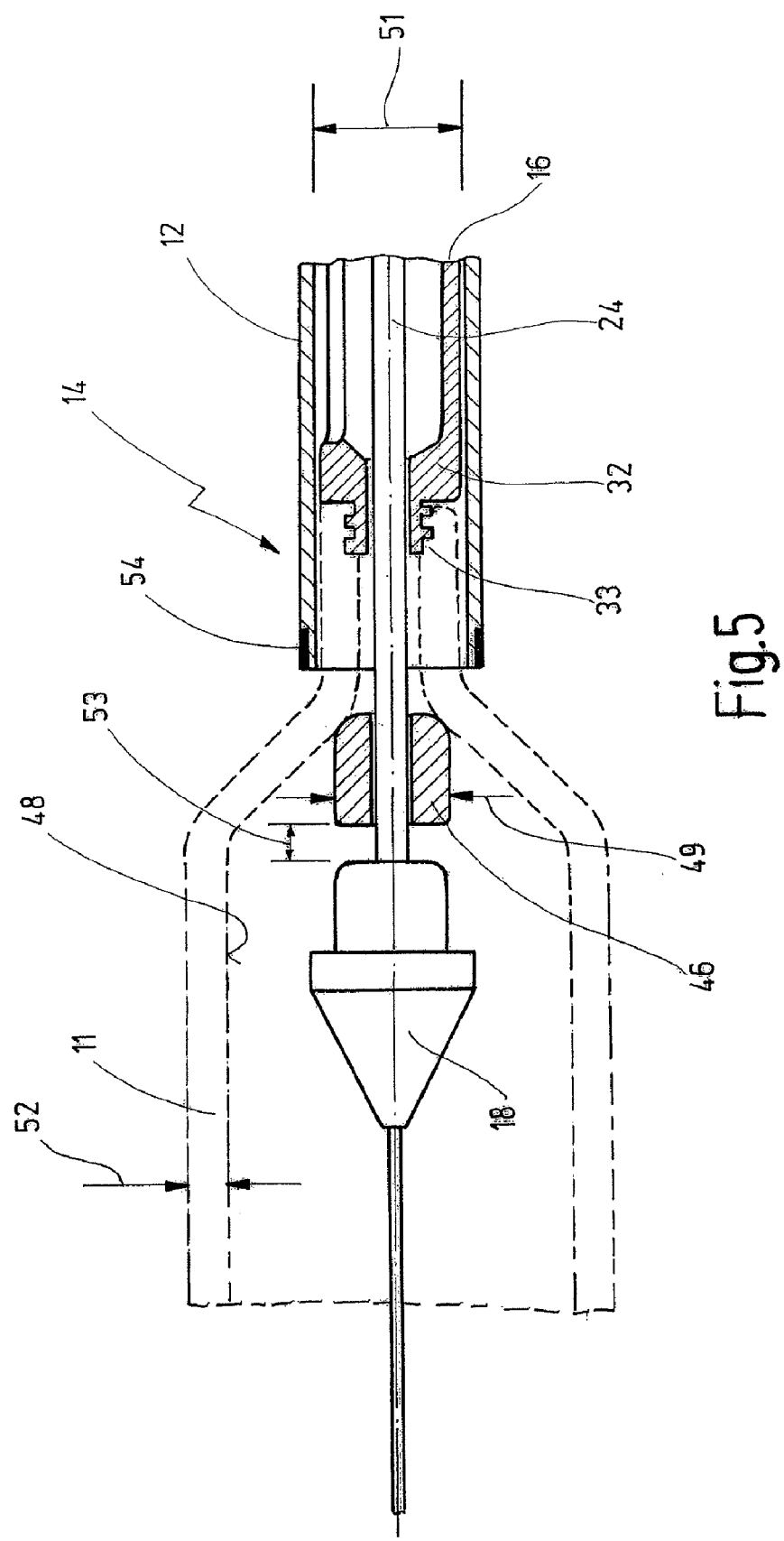
FIG. 5 shows a view similar to FIG. 4, but with the braided stent pulled partially back into the outer sleeve.

FIG. 5 shows, in a view similar to FIG. 4, how the slide body 46 ensures that the braided stent 11 does not become jammed when pulled into the outer sleeve 12. For this purpose, the slide body 46 has an external diameter 49 greater than the difference between the internal diameter 51 of the outer sleeve 12 at the latter's distal end 14 and twice the wall thickness 52 of the braided stent 11.

This arrangement has the effect that, when the braided stent 11 is pulled back in the proximal direction, the slide body 46 remains distally far in front of the distal end 14 of the outer sleeve 12, thereby lessening the danger of the braided stent 11 becoming jammed.

In addition, the slide body 36 is made of a material that has a low coefficient of kinetic friction relative to the inner wall 48 of the braided stent 11, which likewise has the effect that the slide body 26 in FIG. 5 is not pulled in the proximal direction.

However, should the slide body 46 move in the distal direction, its elasticity causes it to be deformed by the braided stent, this deformation energy periodically discharging and allowing the slide body 46 to spring in the distal direction, which leads to an oscillation amplitude indicated by reference number 53.

To ensure that the distal end 14 of the outer sleeve 12 does not widen in the position of the slide body 46 shown in FIG. 5, which, despite the elasticity of the slide body 46, could lead to jamming, the outer sleeve 12 is stiffened at its distal end 14, where it has an X-ray marker 54, which leads to a strengthening of the material of the outer sleeve 12.

In other words, when the braided stent 11 is pulled back into the outer sleeve 12, the slide body 46 oscillates to and fro between the position shown in FIG. 5 and the position shown in FIG. 4 and thus avoids jamming of the braided stent 11, which in this way can be pulled completely back into the outer sleeve 12.

A suitable material for the slide body 46 is Teflon, while the outer sleeve 12 and the stent support 24 are preferably made of thermoplastic, and the inner sleeve 16 can be made partially of high-grade steel.

The diameter 49 is 1.4 mm, for example, the internal diameter 51 is 1.5 mm, and the wall thickness 52 is 0.2 mm. In the expanded state, the braided stent then has a length of 40 mm, for example, and an external diameter of 6 mm with a braid angle of $\alpha=10°$.

Figure 6:
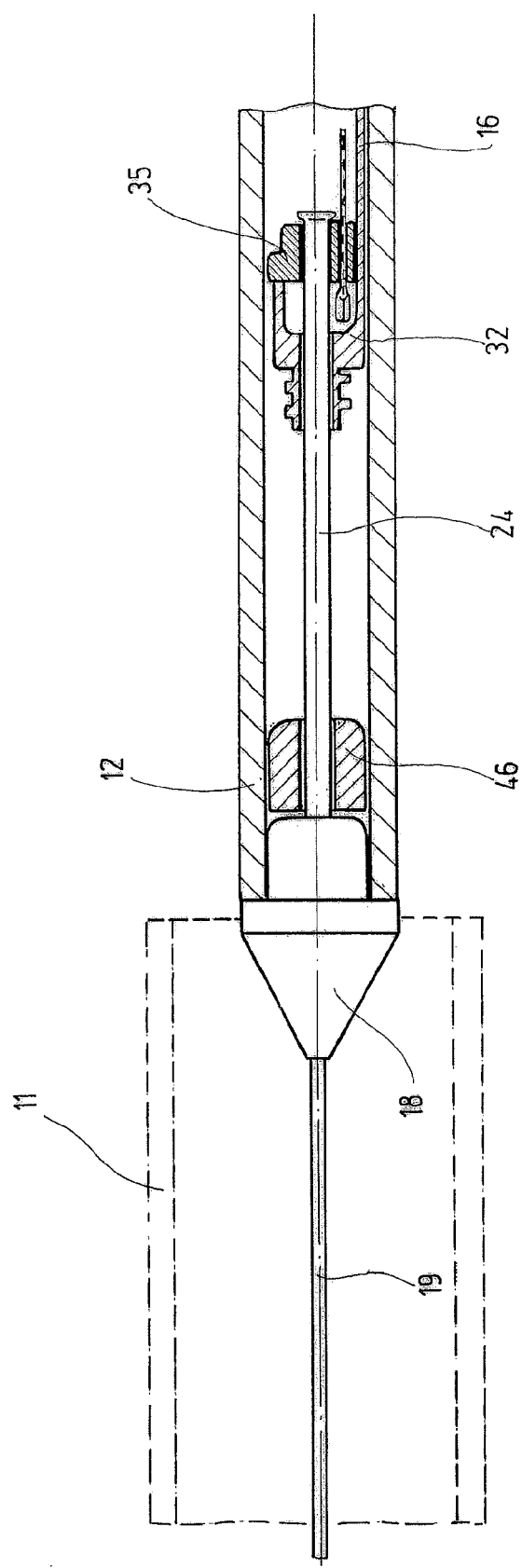
FIG. 6 shows a view similar to FIG. 4, but with the braided stent fully released.

In FIG. 6, the delivery system 10 from FIGS. 4 and 5 is shown in a state in which the braided stent 11 has been fully released. By means of the inner sleeve 16 being pulled back, the distal control block 35 finally comes into contact with the distal end 32 of the inner sleeve 16 and thus pulls the tip 16 back into the outer sleeve 12 over the stent support 24. In this position shown in FIG. 6, the delivery system 10 can now be pulled back out of the blood vessel via the guide wire 19.

In a concrete illustrative embodiment, the delivery system from FIGS. 4 to 6 can comprise an outer sleeve 12 that has an external diameter of 2.0 mm, an internal diameter of 1.55 mm and a length of 1550 mm. The outer sleeve 12 is made of polytetrafluororethylene (PTFE)/polyether block amide (PEBA) and is reinforced or coextruded, for example on the inside from PTFE and on the outside from polyamide (PA).

The inner sleeve 16 then has an external diameter of 1.4 mm, for example, an internal diameter of 0.4 mm, and a length of 200 mm, and is made of a combination of stainless steel (1.4301/1.4310) and a pressure-resistant material such as polyether ether ketone (PEEK).

The stent support 24 has an external diameter of 0.6 mm, an internal diameter of 0.4 mm, and a length of 200 mm and is made of polyimide (PI). The slide body 46 has an external diameter of 1.5 mm, an internal diameter of 0.7 mm, and a length of 2 mm, and it is made of PTFE, PEEK or polyoxymethylene (POM).

Figure 7:
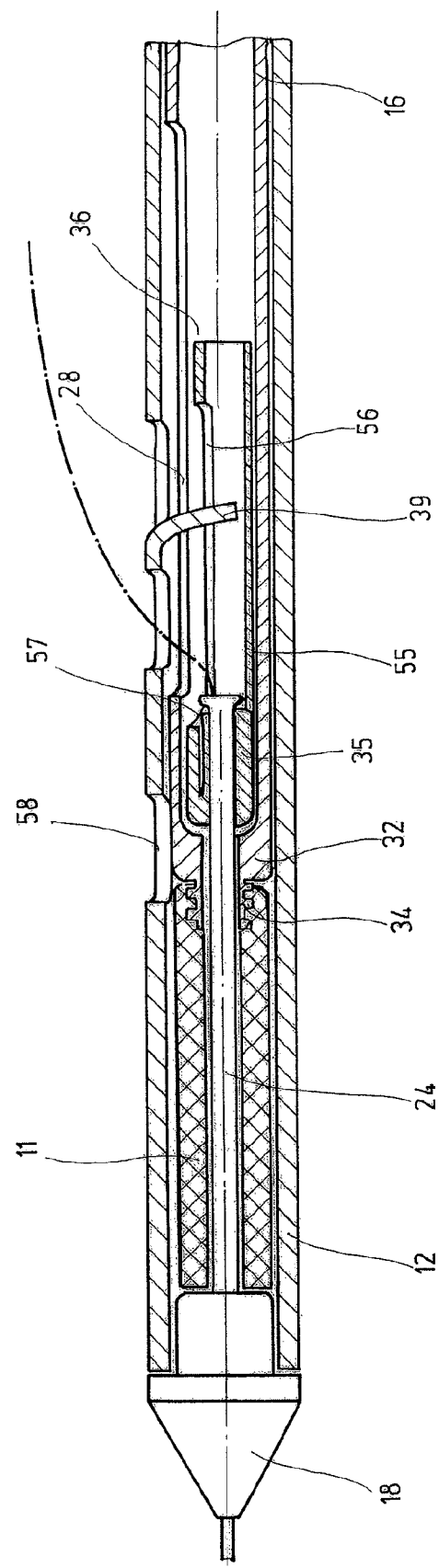
FIG. 7 shows, in a view similar to FIG. 2, a fourth illustrative embodiment of the novel delivery system.

FIG. 7 shows, in a view similar to FIG. 2, a further illustrative embodiment of the novel delivery system.

Figure 8:
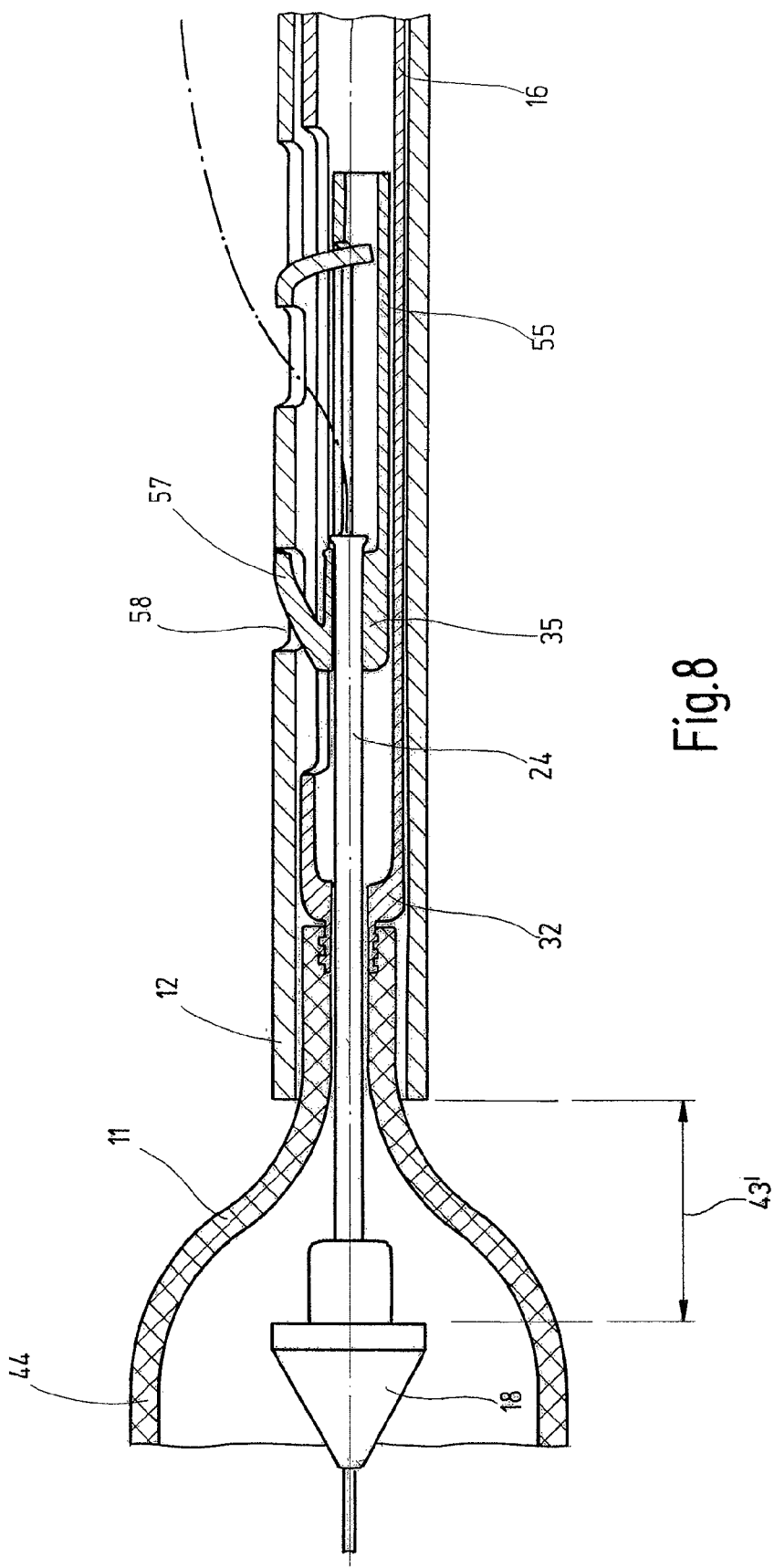
FIG. 8 shows a view similar to FIG. 7, but with the braided stent partially released.
Figure 9:
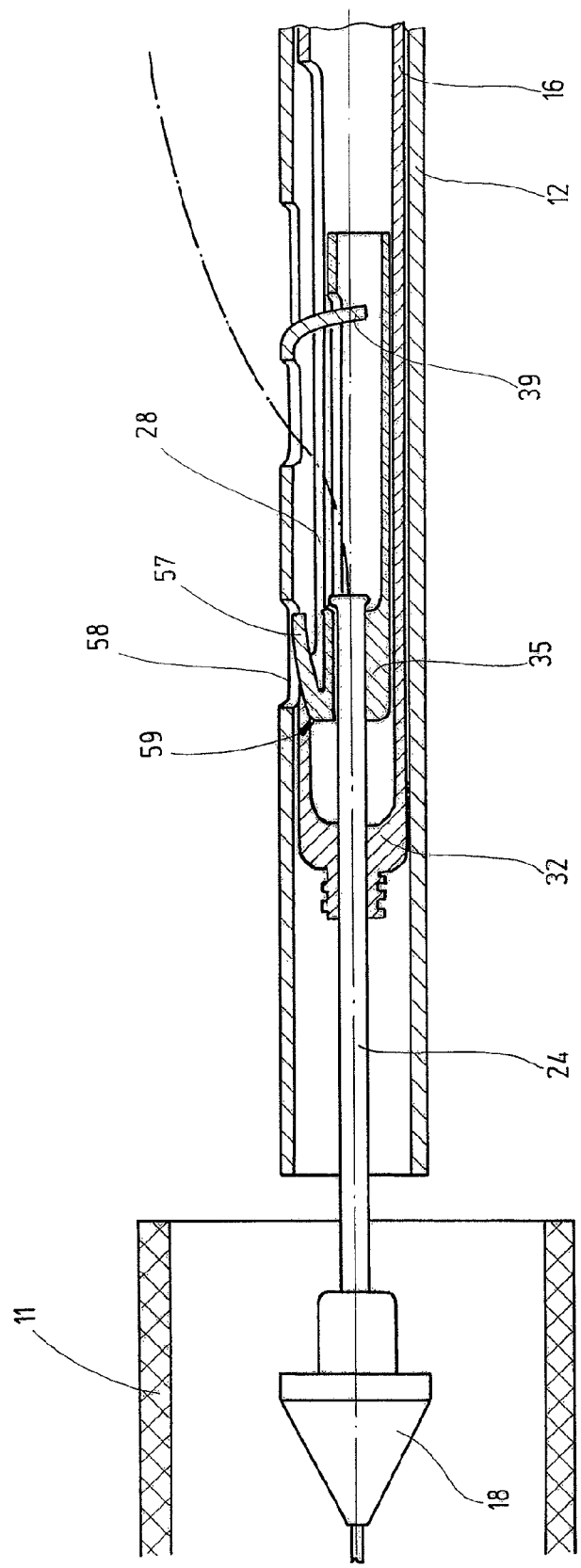
FIG. 9 shows a view similar to FIG. 8, but with the braided stent fully released.

Whereas the slide body 46 in the illustrative embodiment in FIGS. 4 to 6 prevents the braided stent 11 from becoming jammed against the tip 18 when pulled back into the outer sleeve 12, the slide body 46 is not necessary in the illustrative embodiment in FIGS. 7 to 9, since the distal control block 35 and the proximal control block 36 are here formed on a control sleeve 55, which is mounted displaceably in the inner sleeve 16. The control sleeve 55 has a longitudinal slit 56 which is assigned to the longitudinal slit 28 and through which the limit stop 39 engages into the interior of the control sleeve 55. In this way, it is again possible to ensure the maximum path of travel by which the tip 18 can be moved relative to the outer sleeve 12 in the distal direction.

To avoid the tip 18 now inadvertently sliding back in the proximal direction, a further limit stop 57 provided on the distal control block 35 is pressed radially inward, in the position shown in FIG. 7, and bears against the inner sleeve 16. In the position shown in FIG. 8, this further limit stop 57 comes into engagement with a recess 58 in the outer sleeve 12 and thus prevents a movement of the distal control block 35 and therefore of the stent support 24 and tip 18 in the proximal direction.

The position shown in FIG. 8 is adopted as soon as the tip 18 has been moved in the distal direction by a predefined path of travel, which is indicated by reference number 43' in FIG. 8. This predefined path of travel 43' is slightly shorter than the maximum path of travel 43, which is shown in FIG. 4. Even when the inner sleeve 16 is now moved in the proximal direction in the situation shown in FIG. 8, it pulls the braided stent 12 onto the stent support 24. Despite the friction between stent support 24 and braided stent 11, the stent support 24 is not moved in the proximal direction, as this is in fact prevented by the further limit stop 57.

It is also possible, however, to pull the tip 18 back completely into the outer sleeve 12, because, upon further proximal movement of the inner sleeve 16, the latter finally strikes with the distal end 59 of the longitudinal slit 28 against the further limit stop 57 and presses the latter radially inward, with the result that it comes free of the recess 58 again, as is shown in FIG. 9, where the braided stent 11 has already been fully released, such that the tip 18 is now pulled completely back into the outer sleeve 12 in order to be able to remove the delivery system from the vessel.

What is claimed is:

1. A delivery system for implanting a self-expanding braided stent into a blood vessel, comprising:
    an outer sleeve having a distal end and a proximal end, the outer sleeve contacting and holding the stent in a loaded state;
    an inner sleeve arranged within the outer sleeve and having a proximal portion that extends from the proximal end of the outer sleeve, the proximal portion comprising a handling portion, the inner sleeve being displaceable relative to the outer sleeve;
    a stent support comprising a proximal portion and a distal portion, and being displaceable relative to the inner sleeve; and
    a tip arranged at the distal end of the outer sleeve and fixed to the stent support to restrict relative movement between the tip and the stent support,
    wherein the braided stent is arranged on the distal portion of the stent support in the loaded state, and the proximal portion of the stent support extends into the inner sleeve, and
    wherein a locking mechanism is provided between the outer sleeve and the stent support, the locking mechanism restricting movement of the stent support relative to the outer sleeve to a predetermined maximum path of travel in the distal direction wherein the inner sleeve has a longitudinal slit through which a first limit stop connected to the outer sleeve protrudes into the inner sleeve, the limit stop limiting movement of the stent support relative to the outer sleeve in the distal direction to the maximum path of travel.

2. The delivery system as claimed in claim 1, wherein the locking mechanism limits the movement of the stent support relative to the outer sleeve in the proximal direction when the stent support has previously been moved relative to the outer sleeve in the distal direction by a predetermined path of travel.

3. The delivery system as claimed in claim 1, wherein the locking mechanism limits movement of the stent support relative to the outer sleeve in the proximal direction when the stent support has previously been moved relative to the outer sleeve in the distal direction by a predetermined path of travel and wherein an unlocking mechanism is connected to the inner sleeve and, upon proximal movement of the inner sleeve relative to the outer sleeve, movement of the stent support relative to the outer sleeve is permitted.

4. The delivery system as claimed in claim 1, wherein the stent support is connected at its proximal end to a control rod, which extends centrally through the inner sleeve and protrudes at the proximal end from the inner sleeve.

5. The delivery system as claimed in claim 1, wherein the stent support is securely connected to a distal control block, which is mounted displaceably in the inner sleeve and which is connected under tension to a proximal control block mounted displaceably in the inner sleeve, which proximal control block comes into contact with the first limit stop upon movement of the stent support relative to the outer sleeve in the distal direction by the maximum path of travel.

6. The delivery system as claimed in claim 1, wherein the longitudinal slit is assigned a further limit stop, which is connected to the stent support and which comes into contact with a recess on the outer sleeve and limits movement of the stent support relative to the outer sleeve in the proximal direction when the stent support has previously been moved relative to the outer sleeve by a predetermined path of travel in the distal direction.

7. The delivery system as claimed in claim 1, wherein the stent support is securely connected to a distal control block, which is mounted displaceably in the inner sleeve and which is connected under tension to a proximal control block mounted displaceably in the inner sleeve, which proximal control block comes into contact with the first limit stop upon movement of the stent support relative to the outer sleeve in the distal direction by the maximum path of travel, wherein the further limit stop is arranged on the distal control block.

8. The delivery system as claimed in claim 1, wherein the stent support is securely connected to a distal control block, which is mounted displaceably in the inner sleeve and which is connected under tension to a proximal control block mounted displaceably in the inner sleeve, which proximal control block comes into contact with the first limit stop upon movement of the stent support relative to the outer sleeve in the distal direction by the maximum path of travel, and wherein the distal and proximal control blocks are connected to each other by a connecting wire (42) that extends through a guide hole provided in the first limit stop.

9. The delivery system as claimed in claim 1, wherein the stent support is securely connected to a distal control block, which is mounted displaceably in the inner sleeve and which is connected under tension to a proximal control block mounted displaceably in the inner sleeve, which proximal control block comes into contact with the first limit stop upon movement of the stent support relative to the outer sleeve in the distal direction by the maximum path of travel, and wherein the distal and proximal control blocks are formed at opposite ends of a control sleeve, which is mounted displaceably in the inner sleeve and in which a longitudinal slit is provided into which the first limit stop engages.

10. The delivery system as claimed in claim 1, wherein a slide body is longitudinally displaceably arranged on the stent support and lies between the braided stent and the tip when the braided stent is in the loaded state.

11. The delivery system as claimed in claim 1, wherein a slide body is longitudinally displaceablely arranged on the stent support and lies between the braided stent and the tip when the braided stent is in the loaded state, and wherein the slide body has an external diameter that is greater than the difference between the internal diameter of the outer sleeve at its distal end and twice the wall thickness of the braided stent.

12. The delivery system as claimed in claim 1, wherein a slide body is longitudinally displaceablely arranged on the stent support and lies between the braided stent and the tip when the braided stent is in the loaded state, and wherein the slide body is rounded at its proximal end.

13. The delivery system as claimed in claim 1, wherein a slide body is longitudinally displaceablely arranged on the stent support and lies between the braided stent and the tip when the braided stent is in the loaded state, and wherein the slide body is made of a material that has a low coefficient of kinetic friction relative to the inner wall of the braided stent.

14. The delivery system as claimed in claim 1, wherein a slide body is longitudinally displaceablely arranged on the stent support and lies between the braided stent and the tip when the braided stent is in the loaded state, and wherein the slide body is made of an elastic material.

15. The delivery system as claimed in claim 1, wherein a slide body is longitudinally displaceablely arranged on the stent support and lies between the braided stent and the tip when the braided stent is in the loaded state, and wherein the distal end of the outer sleeve is stiffened.

16. The delivery system as claimed in claim 1, wherein a spacer is fixed on the handling portion of the inner sleeve and limits the sliding of the inner sleeve into the outer sleeve.

17. The delivery system as claimed in claim 1, wherein the inner sleeve has a holder at its distal end, via which holder the proximal end of the braided stent is connected under tension to the inner sleeve.

18. The delivery system as claimed in claim 1, wherein the inner sleeve has a holder at its distal end, via which holder the proximal end of the braided stent is connected under tension to the inner sleeve, and wherein the holder has a flange on which the proximal end of the braided stent is fixed by the outer sleeve.

19. The delivery system as claimed in claim 1, wherein a channel for a guide wire extends centrally through the tip and the stent support, the guide wire being guided laterally out of the inner sleeve and the outer sleeve through one or more longitudinal slits.

* * * * *